United States Patent [19]

Dutzmann et al.

[11] Patent Number: 4,847,279
[45] Date of Patent: Jul. 11, 1989

[54] USE OF AZOLYLMETHYL-CYCLOPROPYLCARBINOL DERIVATIVES FOR COMBATING PSEUDOCERCOSPORELLA HERPOTRICHOIDES

[75] Inventors: Stefan Dutzmann, Duesseldorf; Paul Reinecke, Leverkusen; Klaus Böckmann, Cologne, all of Fed. Rep. of Germany

[73] Assignee: Bayer Aktiengesellschaft, Leverkusen, Fed. Rep. of Germany

[21] Appl. No.: 149,247

[22] Filed: Jan. 28, 1988

[30] Foreign Application Priority Data

Feb. 12, 1987 [DE] Fed. Rep. of Germany ....... 3704262

[51] Int. Cl.$^4$ ............................................. A01N 43/64
[52] U.S. Cl. .................................................... 514/383
[58] Field of Search ........................ 548/262; 514/383

[56] References Cited

U.S. PATENT DOCUMENTS

| | | | |
|---|---|---|---|
| 3,991,071 | 11/1976 | Brookes et al. | 548/341 |
| 4,080,462 | 3/1978 | Brookes et al. | 514/399 |
| 4,551,469 | 11/1985 | Parry et al. | 514/383 |
| 4,639,527 | 1/1987 | Lantzsch et al. | 548/262 |
| 4,654,332 | 3/1987 | Parry et al. | 514/383 |

FOREIGN PATENT DOCUMENTS 96307 12/1983 European Pat. Off.
131684 1/1985 European Pat. Off.
180136 5/1986 European Pat. Off.

OTHER PUBLICATIONS

Chem. Abstr., 105:92922q.
Chem. Abst., 105:172469n.
Chem. Abst., 105:172472h.
Derwent Abstract No. 86:120323/19.
European Search Report.

Primary Examiner—Allen J. Robinson
Attorney, Agent, or Firm—Sprung Horn Kramer & Woods

[57] ABSTRACT

Combating Pseudocercosporella herpotrichoides by use of an azolylmethyl-cyclopropyl-carbinol derivative of the formula

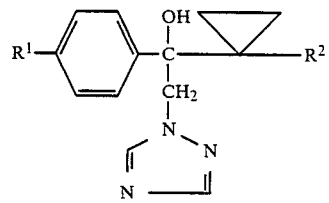

in which
$R^1$ represents fluorine or chlorine and
$R^2$ represents fluorine or chlorine.

3 Claims, No Drawings

USE OF AZOLYLMETHYL-CYCLOPROPYLCARBINOL DERIVATIVES FOR COMBATING PSEUDOCERCOSPORELLA HERPOTRICHOIDES

The invention relates to the use of certain known azolylmethyl-cyclopropyl-carbinol derivatives for combating Pseudocercosporella herpotrichoides. It has already been disclosed that certain azolylmethyl-cyclopropyl-carbinal derivatives have a good fungicidal activity (compare EP-OS (European Published Specification) No. 0,180,136). However, a specific use of these substances against Pseudocercosporella herpotrichoides has not yet been described.

It is furthermore already known that N-[2-(2,4,6-trichlorophenoxy)-ethyl]-N-propyl-1H-imidazole-1-carboxyamide is suitable for combating Pseudocercosporella herpotrichoides (compare U.S. Pat. No. 3,991,071 and U.S. Pat. No. 4,080,462). However, when low amounts are applied, the activity of this substance is not always satisfactory.

It has now been found that azolylmethyl-cyclopropyl-carbinol derivatives of the formula

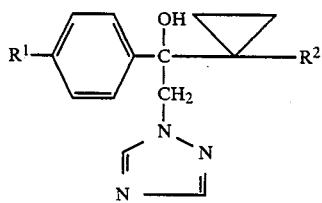

in which
R¹ represents fluorine or chlorine and
R² represents fluorine or chlorine, are particularly suitable for the combating Pseudocercosporella herpotrichoides.

Surprisingly, azolylmethyl-cyclopropyl-carbinol derivatives of the formula (I) show a considerably better activity when used against Pseudocercosporella herpotrichoides than N-[2-(2,4,6-trichlorophenoxy)-ethyl]-N-propyl-1H-imidazole-1-carboxyamide, which is recognized as a particularly effective and chemically similar active compound of the same type of action.

Formula (I) provides a definition of the azolylmethyl-cyclopropyl-carbinol derivatives which can be used according to the invention. The compounds of the following formulae may be mentioned specifically:

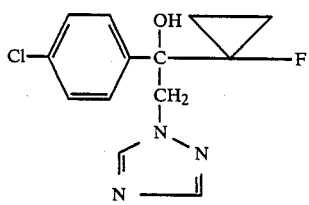

and

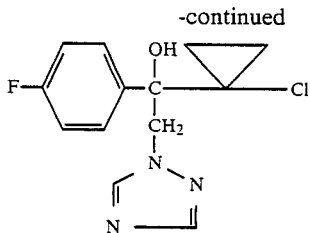

The substances of the formula (I) are known (compare EP-OS (European Published Specification) No. 0,180,136). They can be prepared by a process in which
a) in a first stage cyclopropyl ketones of the formula

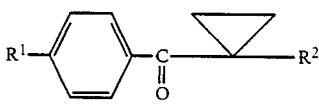

in which
R¹ and R² have the abovementioned meaning, are reacted with dimethyloxosulphonium methylide of the formula $$(CH_3)_2 \overset{\oplus}{S}O \overset{\ominus}{C}H_2 \quad \text{(III)}$$

or with dimethylsulphonium methylide of the formula $$(CH_3)_2\overset{\delta\oplus}{S}\ \overset{\delta\ominus}{C}H_2 \quad \text{(IV)}$$

in the presence of a diluent, such as, for example, dimethylsulphoxide, at temperatures between 10° and 60° C. and (b) the oxiranes thereby formed, of the formula

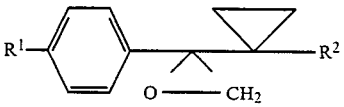

in which
R¹ R² have the abovementioned meaning, are reacted in a second stage with 1,2,4-triazole of the formula

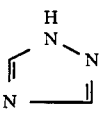

in the presence of a diluent, such as, for example, dimethylformamide or acetoitrile, and in the presence of an acid-binding agent, such as, for example, potassium carbonate or potassium tert.-butylate, at temperatures between 60° and 150° C.

The substances which can be used according to the invention are outstandingly suitable for combating Pseudocercosporella herpotrichoides, the causative organism of stem break disease in cereals. The substances which can be used according to the invention are preferably employed for combating Pseudocercosporella herpotrichoides in wheat and barley.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surfaceactive agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and diethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylenefatty alcohol ethers, for example alkylaryl polyglycol ethers, alkyl sulphonates, alkyl sulphates, aryl sulphonates as well as albumin hydrolysis products; as dispersing agents there are suitable: for example ligninisulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and other growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. The are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The preparation and the use, according to the invention, of the active compounds can be seen from the following examples.

EXAMPLE 1

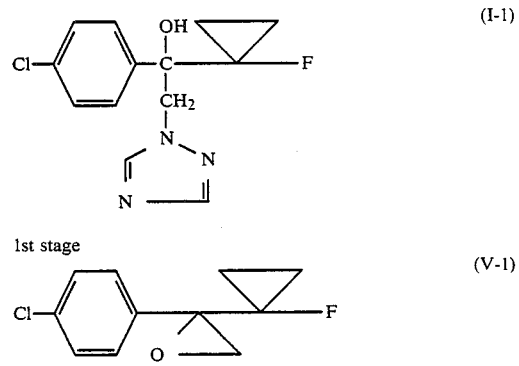

1st stage 120 ml of dry diethylsulphoxide are added dropwise to a mixture of 4.8 g of sodium hydride (80% strength) and 33.7 g of trimethyloxosulphonium iodide at 10° C. and the mixture is subsequently stirred at room temperature for one hour. 29.7 g (0.15 mol) of 1-(4-chlorobenzoyl)-1-fluoro-cyclopropane in 30 ml of dimethylsulphoxide are then added dropwise. The reaction mixture is stirred at room temperature for two days. Thereafter, it is poured onto 400 g of ice and extracted several times with ethyl acetate and the combined organic phases are washed with water, dried over sodium sulphate and concentrated. 24.8 g (78% of theory) of 1-(4-chlorophenyl)-1-(1-fluoro-cyclopropyl)-oxirane are obtained in the form of an oil. Boiling point: 83° C/0.2 mbar.

2nd stage

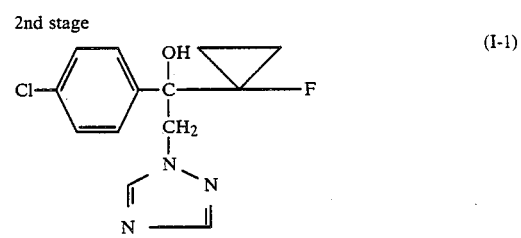

A solution of 117.6 g (0.55 mol) of 1-(4-chlorophenyl)-1-(1-fluoro-cyclopropyl)-oxirane in 120 ml of acetonitrile is added to a boiling mixture of 140 g (2 mol) of 1,2,4-triazole and 78 g of potassium carbonate in 560 ml of acetonitrile and the reaction mixture is heated under reflux for 8 hours. It is concentrated under reduced pressure, the residue is taken up in a mixture of ethyl acetate and water and the organic phase is washed with water, dried over sodium sulphate and concentrated by stripping off the solvent under reduced pressure. The product which remains is subjected to purification by column chromatography on silica gel (mobile phase: chloroform/ethanol=97:3). 92.1 g (60% of theory) of 1-(4-chlorophenyl)-1-(1-fluoro-cyclopropyl)2-(1,2,4-triazol-1-yl)-1-ethanol of melting point 128° C. are obtained.

Preparation of the starting substance

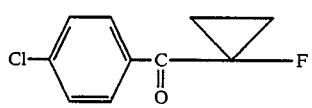
(II-1)

20 g (0.085 mol) of 4-chlorophenyl 1-fluoro-3-chloropropyl ketone are dissolved in 150 ml of tert.butanol and 15 g of potassium tert.-butylate are added in portions. The mixture is subsequently stirred at 40° C. for 2 hours and concentrated in vacuo. The residue is taken up in methylene chloride and water. The organic phase is separated off, dried over sodium sulphate and concentrated in vacuo. The residue is distilled under a high vacuum. 14.4 g (85% of theory) of 1-(4-chlorobenzoyl)-1-fluoro-cyclopropane of boiling point b.p.=75° C./0.1 mbar are obtained.

EXAMPLE 2

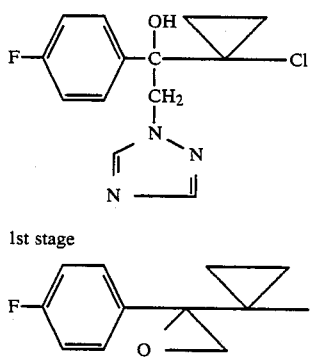

1st stage 1,010 g of dimethyl sulphate are added dropwise to a solution of 665 ml of dimethyl sulphide in 1,300 ml of tert.-butanol at room temperature, while stirring. The mixture is left to stand at room temperature for 14 hours and a solution of 709.5 g (3.6 mols) of 1-(4-fluorobenzoyl)-1-fluoro-cyclopropane in 2,800 ml of tert.butanol is then added. Thereafter, 931 g (16.3 mols) of potassium hydroxide powder are introduced at a temperature of between 20° and 30° C., while stirring. The mixture is subsequently stirred at 30° C. for 3 hours and the excess dimethyl sulphide is then stripped off under reduced pressure. The reaction mixture is then poured onto 2.5 l of 1% strength aqueous hydrogen peroxide solution and extracted several times with ethyl acetate and the combined organic phases are washed with water, dried over sodium sulphate and concentrated. 646 g (91% of theory) of 1-(1-chloro-cyclopropyl)-1-(4-fluorophenyl)oxirane are obtained in the form of an oil. $^1$H-NMR spectrum (60 MHz; CDCl$_3$): $\delta=0.9$–1.4 (m, 4H), $\delta=3.0$ (d, 1H), $\delta=3.15$ (d, 1H) and $\delta=6.9$–7.7 (m, 4H).

2nd stage

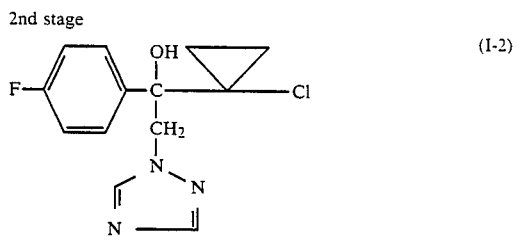

A solution of 27.1 g (0.13 mol) of 1-(1-chlorocyclopropyl)-1-(4-fluorophenyl)-oxirane in 30 ml of absolute dimethylformamide is added dropwise to a mixture of 27.1 g (0.39 mol) of 1,2,4-trizole, 2.9 g of potassium tert.-butylate and 70 ml of absolute dimethylformamide at 50° C. under a nitrogen atmosphere, while stirring. The reaction mixture is heated at 80° C. for 6 hours, while stirring. Thereafter, it is concentrated by stripping off the solvent under reduced pressure, the residue is taken up in a mixture of ethyl acetate and toluene, the mixture is washed with water and dried over sodium sulphate and the solvent is stripped off under reduced pressure. The residue which remains is subjected to purification by column chromatography on silica gel (mobile phase: chloroform : ethanol=98:2). 16.4 g (46% of theory) of 1-(4-fluorophenyl)-1-(1-chloro-cyclopropyl)2-(1,2,4-triazol-1-yl)-1-ethanol of melting point 121° C. are obtained.

Preparation of the starting substance

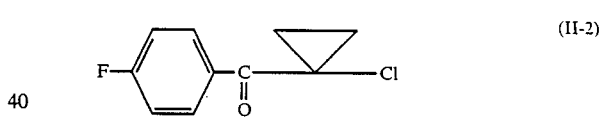

233 g (0.99 mol) of 4-fluorophenyl 1,3-dichloropropyl ketone are dissolved in 300 ml of tert.-butanol and 135 g of potassium tert.-butylate are added in portions. The mixture is substantially stirred at 40° C. for 2 hours and concentrated in vacuo. The residue is taken up in methylene chloride and water. The organic phase is seperated off, dried over sodium sulphate and concentrated in vacuo. The residue is distilled under a high vacuum. 145 g (74% of theory) of 1-(4-fluorobenzoyl)-1-chlorocyclopropane of boiling point 73° C./0.1 mbar are obtained.

EXAMPLE A

Pseudocercosporella test (cereals)/shoot treatment/ field experiment
Cereal variety; winter wheat
Plot size: 1 m$^2$
Number of repetitions: 3
Infestation by: Pseudocercosporella herpotrichoides
The active compounds are used in commercially available formulations when the cereal shoots.
Evaluation is carried out at the time at which the disease symptoms are complete and easy to recognise.
The active compounds, active compound concentrations and experimental results can be seen from the following tables:

TABLE A

Pseudocercosporella test (cereals)/shoot treatment/field experiment

| Active compound | Amount of active compound applied in g/ha | Disease infestation in % of the untreated control |
|---|---|---|
| known: (A) 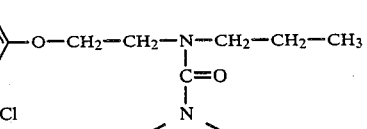 | 250 | 84.1 |
| according to the invention: 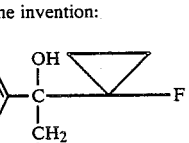 (I-1) | 250 | 43.6 |
| 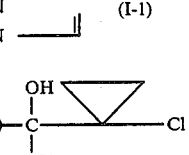 (I-2) | 250 | 34.1 |

It will be appreciated that the instant specification and examples are set forth by way of illustration and not limitation, and that various modifications and changes may be made without departing from the spirit and scope of the present invention.

What is claimed is:

1. A method of combating Pseudocercosporella herpotrichoides which comprises applying to said Pseudocercosporella herpotrichoides a fungicidally effective amount of an azolymethyl-cyclopropyl-carbinol derivative of the formula

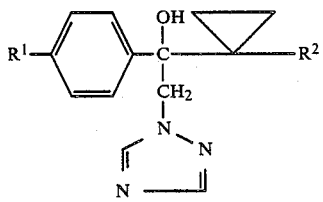

in which
R$^1$ represents fluorine or chlorine and
R$^2$ represents fluorine or chlorine.

2. The method according to claim 1, wherein such derivative is 1-(4-chlorophenyl)-1-(1-fluoro-cyclopropyl)2-(1,2,4-triazol-1-yl)-1-ethanol of the formula

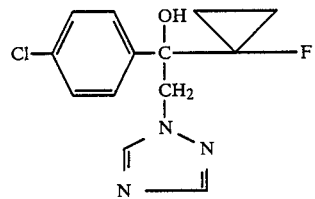

3. The method according to claim 1, wherein such derivative is 1-(4-fluorophenyl)-1-(1-chloro-cyclopropyl)-2-(1,2,4-triazol-1-yl)-1-ethanol of the formula

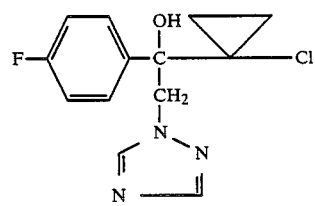

* * * * *